United States Patent
Lofstrom et al.

(10) Patent No.: US 10,025,322 B2
(45) Date of Patent: Jul. 17, 2018

(54) FLUID HANDLING SYSTEM FOR A FLUID FLOW INSTRUMENT

(71) Applicant: CYTONOME/ST, LLC, Boston, MA (US)

(72) Inventors: Christopher D. Lofstrom, Fort Collins, CO (US); Coby S. Hughey, Fort Collins, CO (US); Blair D. Morad, Ipswich, MA (US)

(73) Assignee: CYTONOME/ST, LLC, Bedford, MA (US)

( * ) Notice: Subject to any disclaimer, the term of this patent is extended or adjusted under 35 U.S.C. 154(b) by 133 days.

(21) Appl. No.: 14/713,594

(22) Filed: May 15, 2015

(65) Prior Publication Data

US 2015/0331429 A1    Nov. 19, 2015

Related U.S. Application Data

(60) Provisional application No. 61/994,680, filed on May 16, 2014.

(51) Int. Cl.
*F17D 1/16* (2006.01)
*G05D 7/06* (2006.01)
*G01N 15/14* (2006.01)

(52) U.S. Cl.
CPC ....... *G05D 7/0617* (2013.01); *G01N 15/1404* (2013.01); *G01N 2015/1409* (2013.01); *Y10T 137/0396* (2015.04); *Y10T 137/86107* (2015.04)

(58) Field of Classification Search
CPC ......... Y10T 137/2521; Y10T 137/2705; Y10T 137/3118
See application file for complete search history.

(56) References Cited

U.S. PATENT DOCUMENTS

| | | | |
|---|---|---|---|
| 8,597,573 B2 | 12/2013 | Gilligan | |
| 2008/0216898 A1* | 9/2008 | Grant | A61M 1/1037 137/154 |
| 2008/0249501 A1* | 10/2008 | Yamasaki | A61M 25/0028 604/506 |

* cited by examiner

*Primary Examiner* — R. K. Arundale
(74) *Attorney, Agent, or Firm* — McCarter & English, LLP; David R. Burns

(57) ABSTRACT

A fluid handling system for supplying a working fluid to a fluid flow instrument is disclosed. The system includes a controller configured to receive sensor signals indicative of a deformation of a flexible barrier located between a control fluid volume containing a control fluid and a working fluid volume containing the working fluid. Based on the sensor signals, the controller may send signals to control the operation of a working fluid flow generator in order to regulate or control the fluid characteristic of the working fluid being provided to the fluid flow instrument.

25 Claims, 5 Drawing Sheets

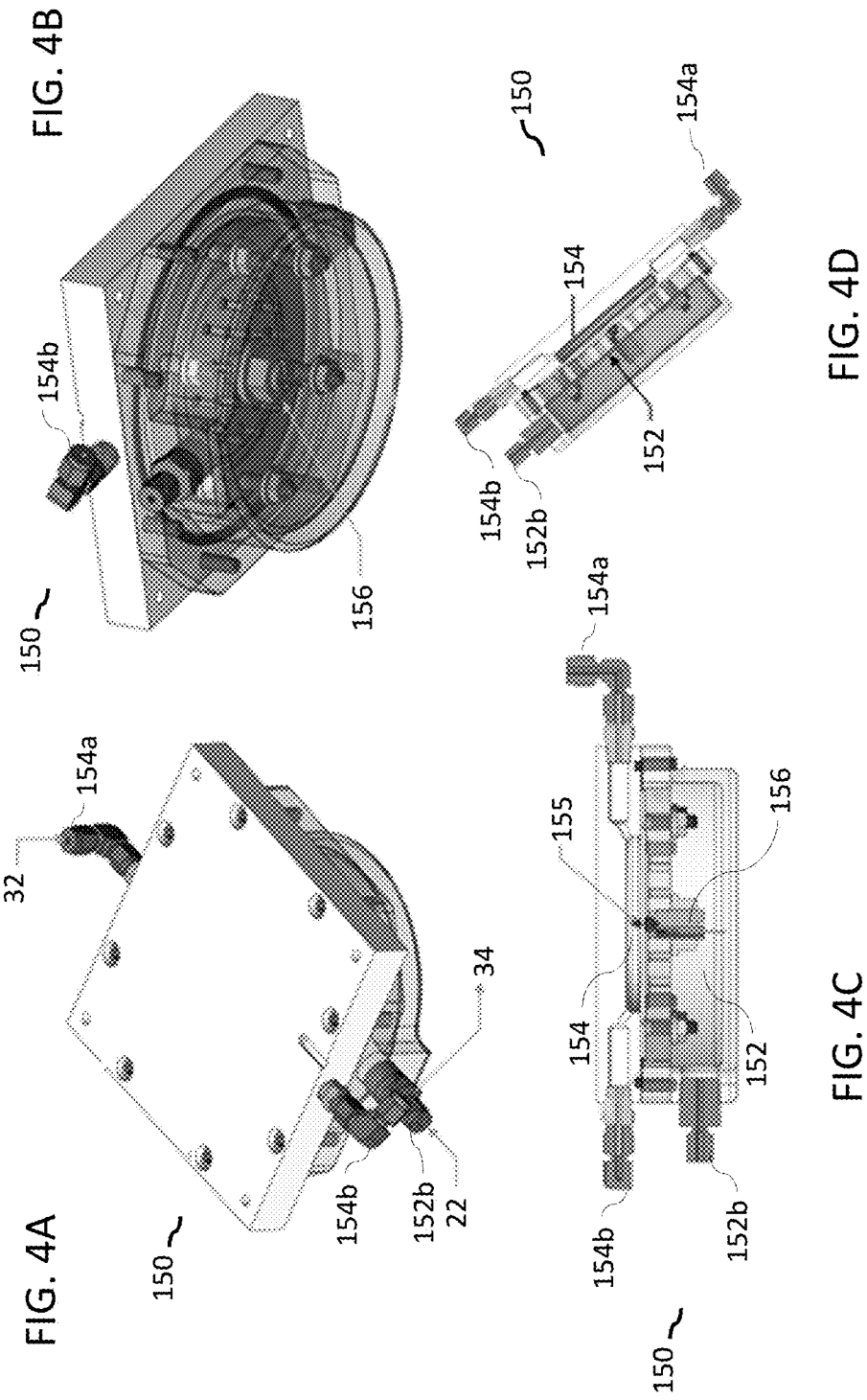

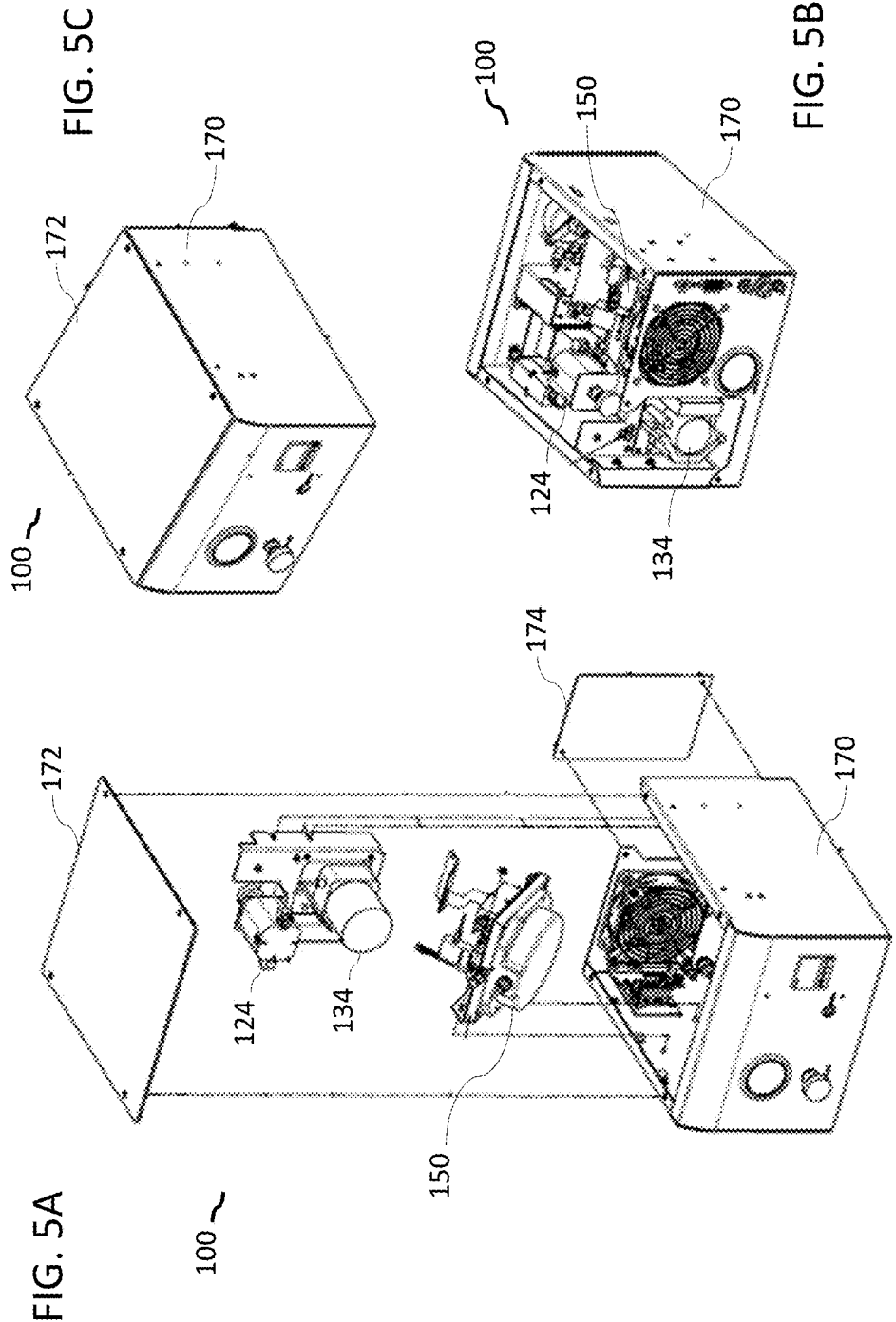

FLUID HANDLING SYSTEM FOR A FLUID FLOW INSTRUMENT

RELATED APPLICATIONS

This application claims the benefit of U.S. Provisional Patent Application Ser. No. 61/994,680, filed on May 16, 2014, the contents of which are incorporated by reference herein in its entirety.

TECHNICAL FIELD

The present disclosure relates generally to a fluid handling system for a fluid flow instrument, and in particular to a sheath fluid delivery system for a particle processing instrument, such as a flow cytometer.

BACKGROUND

Flow cytometers are use in research and clinical applications to analyze the characteristics particles or cells. Typically, in these systems, a particle stream is injected into the center of a laminar sheath flow stream. The combined stream is passed through an interrogation region, where cells of interest are identified. In droplet sorters, the stream may subsequently be divided into droplets, with droplets containing the cells of interest be sorted into separate collection chambers.

A sheath flow delivery system should provide sufficient flow capacity with a substantially invariant flow rate and pressure. The stability of the flow is especially important for sorting applications, because variations in the flow affect the ability of the sorter to efficiently and effectively sort. Additionally, sheath flow delivery systems should provide sheath flow free of bubbles, maintain the sterility of the sheath flow and allow for the replacement of the sheath flow container or reservoir during a sorting operation.

Even further, sheath flow delivery systems should provide stable sheath flow in the presence of variations in the operating environment (e.g., temperature, etc.), variations in the equipment operation (e.g., run-in, voltages, etc.), and variations in the fluid flowing through the system (e.g., pressures, viscosity, etc.).

U.S. Pat. No. 8,597,573 to Gilligan (issued Dec. 3, 2013), which discloses a continuously regulated precision pressure fluid delivery system, is hereby incorporated by reference in its entirety herein. Gilligan discloses a fluid flow characteristic regulator which provides a variable volume flow path in which a fluid flow can be continuously adjusted by a control fluid to regulate at least one fluid flow characteristic of the fluid flow within the variable volume flow path.

SUMMARY

The following presents a general summary of exemplary embodiments in order to provide a basic understanding of at least some aspects of the systems and methods disclosed herein. This summary is not an extensive overview of the present disclosure. Nor is it intended to identify key or critical elements or to delineate the scope of the present disclosure. The following summary merely presents some general concepts of the present disclosure as a prelude to the more detailed description provided below.

According to certain aspects, a method of controlling a fluid handling system to supply a working fluid to a fluid flow instrument is provided. The method may include receiving a compressible control fluid into a control volume of a flow regulator, and supplying a first quantity of a substantially incompressible working fluid having a first pulse peak-to-peak value from a peristaltic pump to a working fluid volume of the flow regulator. The method may further include sending a sensor signal from a sensor to a controller, the sensor signal indicative of a position of a flexible barrier located between the control fluid volume containing the control fluid and the working fluid volume containing the working fluid, and sending a control signal from the controller to the peristaltic pump. The method may also include controlling the speed of the peristaltic pump, and discharging a second quantity of the working fluid having a second pulse peak-to-peak value from the working fluid volume of the flow regulator. The second pulse peak-to-peak value may be less than the first pulse peak-to-peak value. The control signal may be determined, at least in part, as a function of the difference between the sensed position of the flexible barrier and a nominal position of the flexible barrier.

According to other aspects, a fluid handling system including a working fluid flow generator, a flow regulator and a controller is provided. The working fluid flow generator may be configured to supply a pulsed flow of working fluid having a first pulse characteristic to the flow regulator. The flow regulator may include one or more working fluid inlets and one or more working fluid outlets. The flow regulator may be in fluid communication with the working fluid flow generator to receive the pulsed flow of working fluid via the one or more working fluid inlets. Further, the flow regulator may be configured to supply an outlet flow of sheath fluid via the one or more working fluid outlets, the outlet flow having a second pulse characteristic different from the first pulse characteristic. The one or more working fluid outlets may be positioned above the one or more working fluid inlets, such that the working fluid must rise to flow through the flow regulator.

According to even other aspects, a fluid handling system is provided. The fluid handling system may include a working fluid flow generator configured to supply a pulsed flow of working fluid having a first pulse characteristic to a flow regulator and a working fluid flow generator operation sensor configured to sense variations in operation characteristics (temperature, motor speed/rpm, rotor speed/rpm, power draw, acoustics) of the working fluid flow generator. A flow regulator including one or more working fluid inlets and one or more working fluid outlets may also be provided. The flow regulator may be in fluid communication with the working fluid flow generator to receive the pulsed flow of working fluid via the one or more working fluid inlets. Further, the flow regulator may be configured to supply an outlet flow of working fluid via the one or more working fluid outlets. The outlet flow may have a second pulse characteristic attenuated relative to the first pulse characteristic. The fluid handling system may also include a fluid variation sensor configured to sense variations in a working fluid characteristic (pressure, flow in, flow out, temperature, volume, height) within the flow regulator, and a controller configured to receive a fluid variation signal from the fluid variation sensor and configured to receive a working fluid flow generator operation signal from the working fluid flow generator operation sensor. The controller may be configured to compare a change in the signal received from the fluid variation sensor to a change in the signal received from the working fluid flow generator operation signal.

BRIEF DESCRIPTION OF THE DRAWINGS

A more complete understanding of the present disclosure and certain advantages thereof may be acquired by referring to the following description in consideration with the accompanying drawings, in which like reference numbers indicate like features.

FIG. 4A is a top perspective view of a particular embodiment of a flow regulator according to certain embodiments of this disclosure;

FIG. 4B is a bottom perspective view of the flow regulator of FIG. 4A with portions of the housing shown transparent;

FIG. 4C is a cross-sectional side view of the flow regulator of FIG. 4B; and

FIG. 4D is another cross-sectional side view of the flow regulator of FIG. 4B oriented at a 45 degree angle from the horizontal and with the working fluid and control fluid chambers highlighted.

FIG. 5A is an exploded view of a particular embodiment of a fluid handling system;

FIG. 5B is a rear perspective view of the fluid handling system of FIG. 5A with a cover and a back access panel removed; and FIG. 5C is a front perspective view of the fluid handling system of FIG. 5A.

DETAILED DESCRIPTION

In the following description of various example embodiments, reference is made to the accompanying drawings, which form a part hereof, and in which are shown by way of illustration various example devices, systems, and environments in which aspects of exemplary embodiments disclosed herein may be practiced. It is to be understood that other specific arrangements of parts, example devices, systems, and environments may be utilized and structural and functional modifications may be made without departing from the scope of the present disclosure.

Generally, a fluid handling system as disclosed herein includes both devices and methods for the delivery of fluid to a fluid flow instrument. The fluid handling system provides a consistent, stable, and controlled flow of fluid to the instrument.

Thus, according to aspects of this disclosure, the fluid handling system may be in fluid communication with a fluid flow instrument to provide intermittent or continuous delivery of a fluid to the instrument. The fluid flow instrument may be a particle processing instrument, for example, a flow cytometer, a droplet sorter, a microfluidic chip, a liquid chromatograph, or other flow-through analytical instrument. The fluid may be a sheath fluid, a sample fluid, a reagent fluid, a flushing fluid, a cleaning fluid, etc.

For example, during operation of a typical flow cytometer, a sheath fluid stream and a sample fluid stream are provided to the instrument. The sample stream and the sheath fluid stream join within the flow cytometer to form an entrained stream. The fluid flow parameters of the sheath fluid (and of the sample fluid) entering the cytometer affect the performance of the cytometer.

In jet-in-air flow cytometers, the entrained stream passes through a nozzle to form droplets. A steady state oscillation of the nozzle in conjunction with a steady state supply of sheath fluid and sample fluid may establish a steady state oscillation of the fluid stream. In turn, this steady state oscillation of the fluid stream may generate a steady stream of droplets with a stable droplet break-off point. The droplets may be interrogated and differentiated based on certain characteristics of particles located within the droplets. An electric charge may be applied to select droplets so that these droplets may be deflected as they fall past charged plates and collected.

Because certain operating characteristics (e.g., formation of droplets, droplet break-off point, or the like) of the flow cytometer may be influenced by the sheath fluid flow rate, the sample fluid flow rate, the sheath fluid pressure, the sample fluid pressure, or the like, it is desirable to control these fluid input parameters. The fluid handling systems described herein advantageously provide fluid flow(s) to the fluid flow instrument that have smooth, stable flow parameters, thereby resulting in a more consistent operation of the fluid flow instrument.

Figure 1:
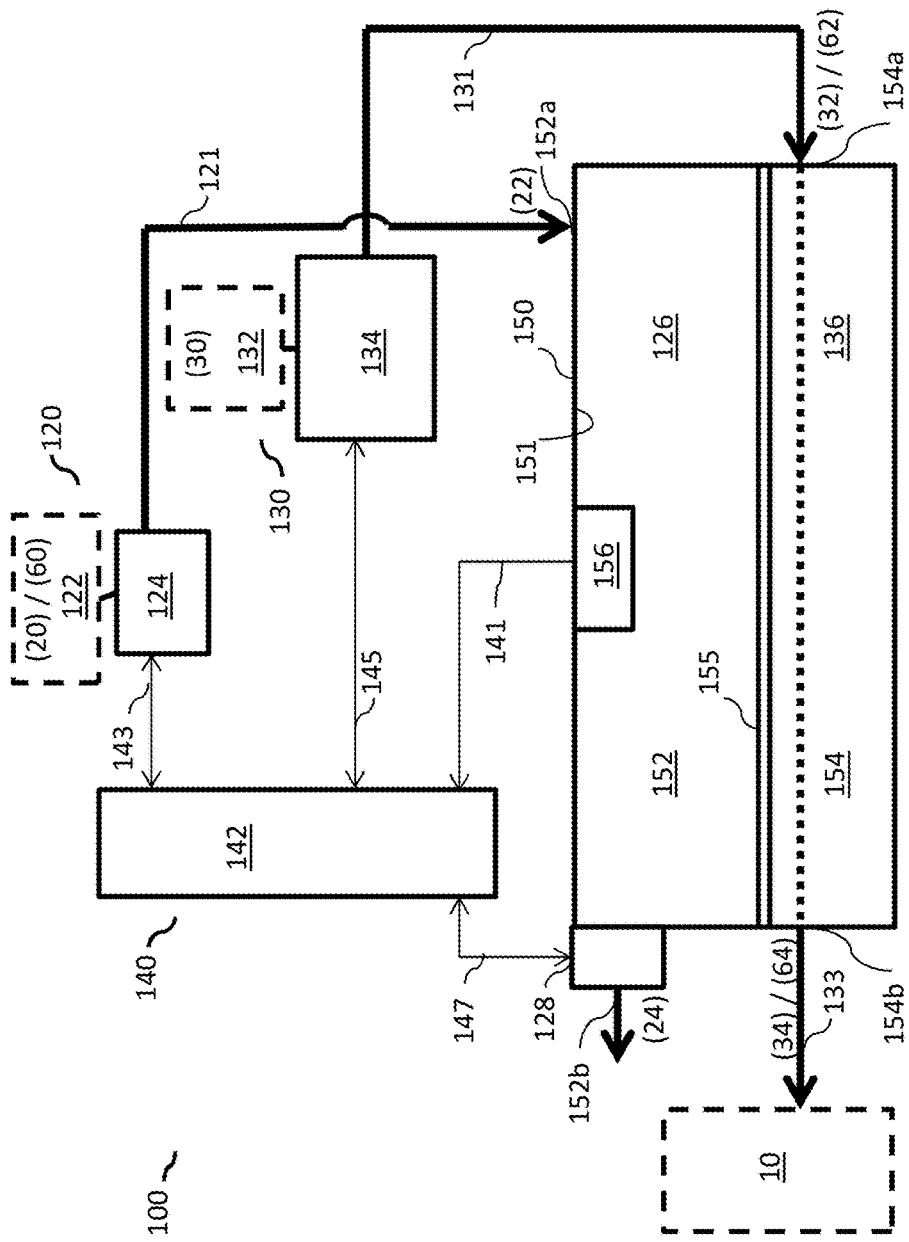
FIG. 1 is a block diagram of a fluid handling system according to an embodiment of this disclosure.

Referring to FIG. 1, an embodiment of a fluid handling system 100 that reduces the variation in one or more fluid flow parameters of a working fluid provided to a fluid flow instrument 10 (e.g., a particle processing instrument) is illustrated. For example, the fluid flow instrument 10 may receive a relatively stable working fluid flow stream 34 from the fluid handling system 100. In this embodiment, the fluid handling system 100 uses a control fluid 20 to regulate at least one fluid flow parameter of a working fluid 30. The working fluid 30 enters a flow regulator 150 as a relatively variable working fluid flow stream 32 and exits the flow regulator as a relatively stable working fluid flow stream 34. The regulated or controlled working fluid flow stream 34 output from the fluid handling system 100 is suitable for input into fluid flow instruments 10 that are operationally sensitive to input fluid parameters and/or variations in the input fluid parameters. The term "working fluid" refers to any fluid that is used as input to the fluid flow instrument. As a non-limiting example, the working fluid 30 may be a sheath fluid. As another non-limiting example, the working fluid 30 may be a sample fluid.

Figure 2:
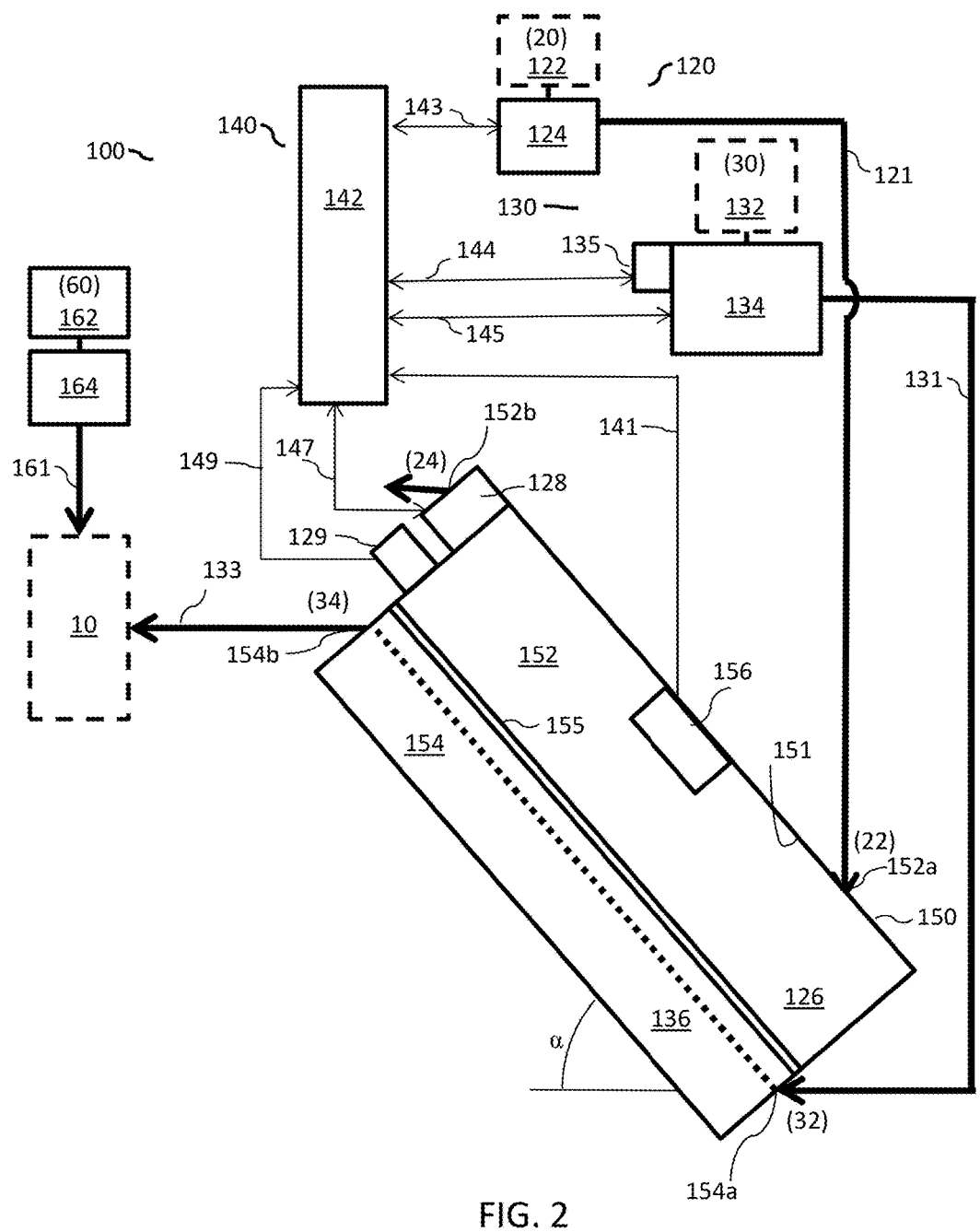
FIG. 2 is a block diagram of a fluid handling system according to another embodiment of this disclosure.

Now referring to FIGS. 1 and 2, a fluid handling system 100 may be fluidically coupled to a fluid flow instrument 10. The fluid handling system 100 may include a control fluid flow system 120, a working fluid flow system 130, a control system 140 and a flow regulator 150. The flow regulator 150, in conjunction with the control system 140, regulates or controls one or more fluid flow parameters of the working fluid 30. Specifically, the flow regulator 150, in conjunction with the control system 140, may adjust one or more fluid flow parameters of the working fluid 30 by adjusting one or more parameters of the control fluid flow 22 and/or working fluid flow 32.

Referring to FIGS. 1 and 2, a control fluid flow system 120 may include a control fluid regulator 124, a first control fluid flow path 121, a regulated control fluid volume 126, and a pressure release system 128. The components of the control fluid flow system 120 are in fluid communication with each other. The control fluid flow system 120 may be configured to be coupled to, and in fluid communication with, a control fluid supply 122. The control fluid supply 122 may contain a control fluid 20. The control fluid 20 may be a gas. In a preferred embodiment, the gas may be air. Depending upon the application, other control fluids 20 (whether a gas or a liquid) may be provided. The control fluid supply 122 may include a pressurizing component. According to certain embodiments, the control fluid supply 122 may include a pump, an air compressor, laboratory air, etc. According to other embodiments, the control fluid supply 122 may be, for example, a compressed tank of gas.

The control fluid regulator 124 may be configured to be coupled to, and placed in fluid communication with, a pressurized control fluid supply 122. The control fluid regulator 124 may control the pressure, flow rate, etc. of the control fluid 20 supplied by the control fluid supply 122. For example, the control fluid regulator 124 may accept control fluid 20 at a first pressure from any of various control fluid supplies 122 (e.g., lab air at 120 psi (8.3 bar), 100 psi (6.9 bar), 80 psi (5.5 bar), etc.) and provided a regulated control fluid flow 22 at a second pressure (e.g., at up to approximately 20 psi (1.4 bar), 30 psi (2.1 bar), 40 psi (2.7 bar), 45 psi (3.1 bar), 50 psi (3.4 bar), etc.). As used herein, the term "approximately" means plus/minus 5%, unless otherwise limited.

In any event, control fluid flow system 120 provides a pressurized flow of control fluid 20 via the first control fluid flow path 121 to flow regulator 150. Specifically, a pressurized control fluid flow 22 is supplied to a regulated control fluid volume 126 defined within flow regulator 150.

A pressure release system 128 may be provided in fluid communication with the regulated control fluid volume 126 of flow regulator 150. A control fluid release flow 24 may be released from the regulated control fluid volume 126 via pressure release system 128, e.g., a control fluid regulator valve.

As would be known to persons of ordinary skill in the art given the benefit of this disclosure, the control fluid flow system 120 may include one or more fluid flow filters, valves, manifolds, gauges, etc. For example, an air pressure gauge (not shown) may be positioned downstream of the control fluid regulator 124 to provide an operator with a real-time readout of the control fluid pressure. As another example, referring to FIG. 2, an air pressure transducer 129 may be in fluid communication with the regulated control fluid volume 126 defined within flow regulator 150 in order to provide a signal 149 reflecting the pressure within the regulated control fluid volume to the control system 140 and/or to a display.

Even further, the pressure handling system 100 may include a vacuum system (not shown) configured for connection, for example, to a waste path.

Still referring to FIGS. 1 and 2, a working fluid flow system 130 may include a working fluid flow generator 134, a first working fluid flow path 131, a regulated working fluid flow volume 136, and a second working fluid flow path 133. The components of the working fluid flow system 130 are in fluid communication with each other. The working fluid flow system 130 may be configured to be coupled to, and placed in fluid communication with, a working fluid supply 132. Specifically, the working fluid flow generator 134 may be configured to be coupled to, and placed in fluid communication with, the working fluid supply 132. A working fluid 30 may be contained within the working fluid supply 132. In general, the working fluid supply 132 may be of any configuration capable of containing an amount of working fluid 30. In certain applications, the working fluid supply 132 may be a fluid tank, a replaceable rigid container such as a bottle made of plastic or glass, or a replaceable flexible container such as a fluid bag. In a preferred application, the working fluid 30 is a sheath fluid. Depending upon the application, other working fluids 30 (whether a gas or a liquid) may be provided.

Working fluid flow system 130 provides a pressurized flow of working fluid 30 via the first working fluid flow path 131 to working fluid flow regulator 150. Specifically, a pressurized working fluid flow 32 is supplied to a regulated working fluid flow volume 136 defined within working fluid flow regulator 150. The pressurized working fluid flow 32 has one or more flow parameters or characteristics that are relatively variable, and typically, not sufficiently stable to use as an input to flow-sensitive fluid flow instruments. The flow regulator 150 is designed to reduce and/or substantially eliminate these undesirable variations in the flow parameters associated with working fluid flow 32 and provide a smoother working fluid flow 34 having more consistent, less variable flow parameters. Thus, a substantially invariant, regulated or controlled working fluid flow 34 exits from fluid flow regulator 150 and is provided to fluid flow instrument 10 via second working fluid flow path 133.

In accordance with certain embodiments and referring for example to FIG. 2, a sample fluid 60 may be provided within a sample fluid source 162. A sample fluid flow generator 164 may provide the sample fluid 60 to the fluid flow instrument via a sample fluid flow path 161. According to certain embodiments, the sample fluid flow generator 164 may be a pressure source such as a peristaltic pump. A stream of the sample fluid 60 may join the working fluid flow 34, for example, a sheath fluid, in the fluid flow instrument 10 to form an entrained stream.

Alternatively, the working fluid of FIGS. 1 and 2 may be a sample fluid 60 (rather than a sheath fluid). Thus, a fluid handling system 100 may be provided to reduce any undesirable variation in one or more fluid flow parameters of a sample fluid provided to a fluid flow instrument 10 (e.g., a particle processing instrument). For example, the fluid flow instrument 10 may receive a relatively stable sample fluid flow stream 64 from the fluid handling system 100. In this embodiment, the fluid handling system 100 may use a control fluid 20 to regulate at least one fluid flow parameter of a sample fluid 60. The sample fluid 60 enters a flow regulator 150 as a relatively variable sample fluid flow stream 62 and exits the flow regulator as a relatively stable sample fluid flow stream 64. The regulated or controlled sample fluid flow stream 64 output from the fluid handling system 100 is suitable for input into a fluid flow instrument 10 that is operationally sensitive to input fluid flow parameters and/or variations. According to some embodiments, a one or more fluid handling systems 100 (e.g., a fluid handling system for sheath fluid and a fluid handling system for sample fluid) may be provided in a common housing.

Again referring to FIGS. 1 and 2, the working fluid flow generator 134 generates a pressurized working fluid flow 32 from the working fluid supply 132. The working fluid flow generator 134 may be a pump such as a single piston, dual piston, proportioning valve, diaphragm, peristaltic, etc. Optionally, the working fluid flow generator 134 may be a pressure source regulated by a valve or other fluid limiting component.

Figure 3:
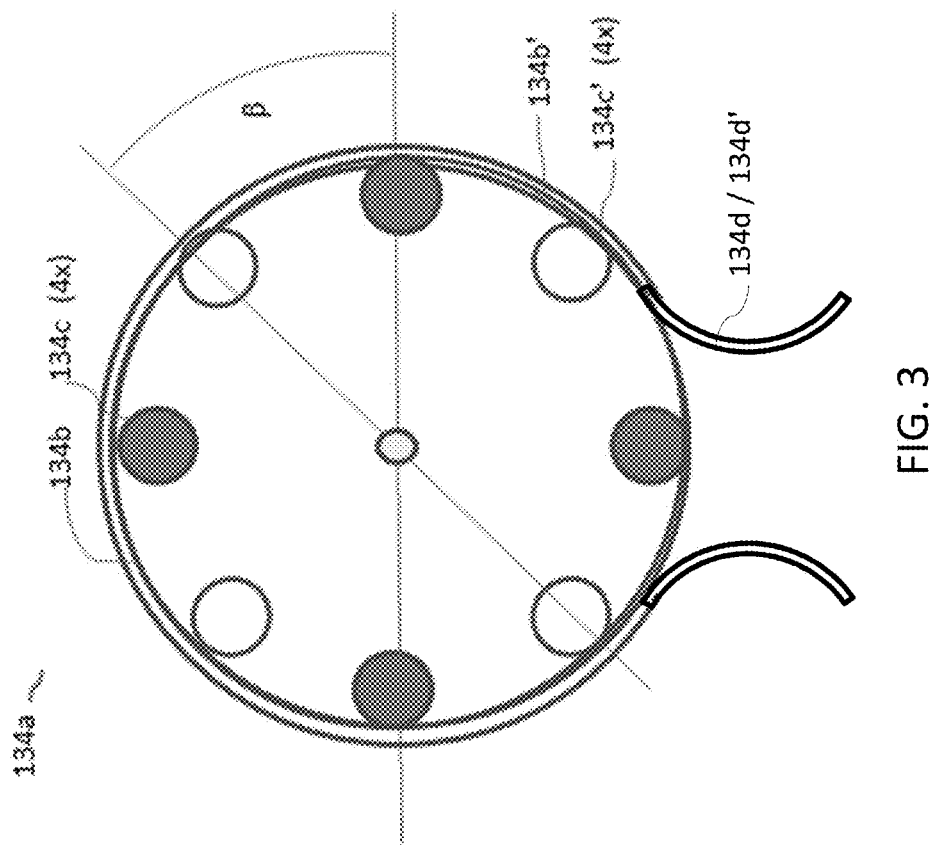
FIG. 3 is a plan view schematic of a portion of a peristaltic pump illustrating a dual rotor configuration according to certain embodiments of this disclosure.

In preferred embodiments and referring to FIG. 3, a pump 134a may be a positive displacement pump such as a peristaltic pump. Typically, a peristaltic pump has a rotor 134b (or head) mounted on a drive shaft coupled to a motor. Preferably the rotor is geared down, so that, for example, the motor may rotate at approximately 10 times the speed of the rotor. The rotor is provided with a plurality of rollers or shoes 134c at the outer circumference of the rotor 134b. The shoes 134c may be integrally formed with the rotor 134b or may be formed separately from and subsequently attached to the rotor. At least one flexible tube 134d is fitted between the rotor 134b and a wall of the pump casing. The shoes 134c compress and, in general, pinch closed the flexible tube(s) 134d. As the rotor 134b turns, the shoes 134c travel along the length of the flexible tube 134d that is fitted around the rotor 134b, thereby sequentially pinching and then releasing portions of the tube 134d. Fluid within the tube 134d is forced ahead of the traveling pinched portions and through the tube. When the tube 134d opens to its natural state after the passing of the shoes 134c, fluid is drawn into the tube 134d. The pump 134a may have a known flow rate to pump speed ratio, and thus, control of the speed of the pump drive shaft may correspond to a control of the flow rate of the fluid.

As a non-limiting example, the rotor 134b may be fitted with four evenly spaced shoes 134c. In general, the rotor 134b may have any number of shoes 134c associated therewith. Further, the shoes 134c need not be evenly spaced.

In certain preferred embodiments and still referring to FIG. 3, the pump 134a may be a dual-head or multi-head peristaltic pump. In other words, peristaltic pump 134a may be fitted with more than one rotor 134b, 134b' or head on a common drive shaft (i.e., a dual rotor configuration). Each rotor 134b, 134b' may be fitted with a plurality of spaced shoes or rollers 134c, 134c', respectively. In particularly preferred embodiments, the shoes 134c of the first rotor 134b may be staggered or offset by an angle β with respect to the shoes 134c' of the second rotor 134b'. In other words, a peristaltic pump 134a with an offset dual rotor configuration may be designed so that one rotor produces a maximum flow rate as the other rotor's flow rate reduces to its minimum. The upstream fluid flow channel may be split into two flexible tubes 134d, 134d' upstream of the pump 134. Each of the two flexible tubes 134d, 134d' may be associated with one of the two rotors 134b, 134b' such that the pulsed flow for the two flexible tubes 134d, 134d' is staggered. By combining the output from both flexible tubes into a common fluid flow channel downstream of the pump, the effect of the peristaltic pulsing may be significantly lessened. Alternatively, the pump may be a peristaltic pump having at least two rotors operating at a relative phase to one another.

Referring now to FIG. 3, for example, should each rotor 134b, 134b' have four evenly spaced shoes 134c, 134c' (i.e., positioned 90 degrees apart), respectively, a pair of such rotors 134b, 134b' may be oriented on the common drive shaft with the shoes 134c, 134c' offset or staggered such that the shoes 134c of the first rotor 134b are at an angle β of approximately 45 degrees from the shoes 134c' of the second rotor 134b'. In other embodiments, each rotor 134b, 134b' may have any number of shoes 134c, 134c' and the angular offset or spacing between the shoes 134c of the first rotor 134b and the shoes 134c' of the second rotor 134b, 134b' may be greater than or less than 45 degrees. Each of the plurality of rotors 134b, 134b' may have the same diameter. Optionally, the rotors 134b, 134b' may have different diameters. Further, each rotor 134b, 134b' may be associated with one or more flexible tubes 134d, 134d'.

In yet further embodiments, the pump may be fitted with two rotors (as in FIG. 3) or with more than two rotors. For example, in some embodiments, the pump may be fitted with three or more rotors, each fitted with a plurality of spaced shoes or rollers which are staggered or offset relative to the spaced shoes or rollers of the other rotors.

Other schemes for staggering the pulses of a plurality of flows may include, for example, having two independent peristaltic pumps where a controller's algorithm monitors and adjusts the phase of one pump relative to the other pump. The control algorithm may be based on minimizing pressure pulses measured downstream. As another possible example, two flexible tubes may be run along a single rotor, wherein the two flexible tubes have different lengths between the rotor and a downstream junction. In certain embodiments, the difference in length would equal a half-pulse width.

According to certain embodiments, the working fluid flow generator 134 may be a peristaltic pump 134a providing a nominal output pressure of greater than approximately 20 psi, greater than approximately 30 psi, greater than approximately 40 psi, greater than approximately 50 psi, or even greater than approximately 60 psi. As a non-limiting example, the working fluid flow generator 134 may be a peristaltic pump 134 providing a nominal output pressure ranging from approximately 30 psi to approximately 50 psi. Further, the working fluid flow generator 134 may be a peristaltic pump 134a providing a nominal output pressure of approximately 40 to 45 psi with an output pulse fluctuation of up to approximately 8 to 9 psi (peak-to-peak). In some embodiments, the peristaltic pump 134a may provide a nominal output pressure of approximately 40 to 50 psi with an output pulse fluctuation of up to approximately 4 psi (peak-to-peak).

In one embodiment, a dual-head peristaltic pump 134a outfitted with 1.6 mm inner diameter tubing may provide a nominal output pressure of approximately 40 to 50 psi with an output pulse fluctuation of approximately 4 psi (peak-to-peak). A two-channel Watson Marlow peristaltic pump, model no. 400F/N2 may be suitable for certain applications. Other configurations of pumps having other nominal output pressures and other peak-to-peak output pulse fluctuations may be suitable, as would be known to a person of ordinary skill in the art, given the benefit of this disclosure.

Higher working fluid (e.g., sheath fluid) pressures may advantageously allow the fluid flow instrument 10 to run at higher sample event rates with relatively low coincidence rates. Further, for droplet sorters, operating at relatively high sheath fluid pressures advantageously provides the capability to generate droplets at higher frequencies, thereby resulting in higher sort rates. Additionally, operating the fluid handling system 100 at such relatively high pressures means that the pressure pulses due to the working fluid flow generator 134 are a relatively small percentage of the pressure within the flow regulator.

The working fluid flow generator 134 may be sized to provide any suitable flow rate of working fluid 30. According to certain embodiments, the working fluid flow generator 134 may be configured to provide a flow rate of up to approximately 50 mL/min. In preferred embodiments, for example for use with a droplet sorter, a working fluid flow generator 134 may be capable of providing a flow rate of ranging from 1 mL/min up to approximately 30 mL/min. As a non-limiting example, a peristaltic pump 134a providing sheath fluid to a single droplet sorter may be configured to provide a flow rate of between approximately 3 mL/min to approximately 20 mL/min.

As would be known to persons of ordinary skill in the art given the benefit of this disclosure, the control fluid flow system 120 and/or the working fluid flow system 130 may include one or more fluid flow filters, valves, manifolds, gauges, quick disconnect fittings, etc. For example, a 0.2 micron filter (not shown) may be positioned downstream of the working fluid supply 132 and upstream of the fluid flow generator 134. The control fluid system may be provided with tubing fluidically coupling the components, the tubing having an inner diameter less than 0.032 inches. The working fluid control system may be provided with tubing fluidically coupling the components, the tubing having an inner diameter less than 0.064 inches. According to certain embodiments, the tubing may be flexible, pinch tubing and the valves may be pinch valves.

Again referring to FIGS. 1 and 2, the fluid handling system 100 may include a control system 140. The control system 140 may include a fluid controller 142 that runs a control application. The fluid controller 142 is in communication with the flow regulator 150. Specifically, the fluid controller 142 may receive signals 141 from a sensor 156 associated with the flow regulator 150.

Further, the fluid controller 142 may be in communication with the control fluid regulator 124 to regulate or control a flow parameter of the control fluid 20 flowing from the control fluid supply 122. For example, the fluid controller 142 may operate to control the flow rate of the control fluid 20 from the control fluid supply 122. In general, the fluid controller 142 may operate to adjust the pressure, volume, rate, or other control fluid characteristic of the control fluid 20. Further, the fluid controller 142 may operate to intermittently or continuously deliver control fluid 20 from the control fluid supply 122 to the control fluid flow path 121. The control fluid regulator 124 may be a gas pressure regulator or other regulator as known in the art.

Even further, the fluid controller 142 may be in communication with the working fluid flow generator 134 to regulate or control a flow parameter of the working fluid 30 flowing from the working fluid supply 132. For example, the fluid controller 142 may operate to control the flow rate of the working fluid 30 from the working fluid supply 132. In general, the fluid controller 142 may operate to adjust the pressure, volume, rate, or other working fluid characteristic of the working fluid 30. For example, the fluid controller 142 may operate to intermittently or continuously supply working fluid 30 from the working fluid supply 132 to the working fluid flow path 131. As described above, the working fluid flow generator 134 may be a pump. As a non-limiting example, the fluid controller 142 may control the speed of the pump's motor.

The fluid controller 142 may be implemented as a computer which receives, analyzes and/or sends signals to or sensors, displays, regulators, valves, and other active components of the fluid handling system. The computer may be a conventional computer, a distributed computer, or any other type of computer which may contain all or a part of the elements described or shown to accomplish the functions described herein. The computer may include an operating system and a controller application. Functionalities of the control fluid controller application may be implemented as an application specific integrated chip (ASIC) or on a programmable gate array (FPGA), or the like. The controller application loaded onto the computer produces a machine.

In preferred embodiments, fluid controller 142 may be implemented as a proportional-integral-derivative (PID) controller. The PID controller may be programmed to send to and/or receive signals from the flow regulator 150, from the control fluid regulator 124, and from working fluid flow generator 134. Further, the PID controller may be programmed to send and/or receive signals continuously from any of these components. The term "continuously" in this context refers to commands being updated at least twice per second, and preferably approximately 3 times or more per second. As one example, an Omega Engineering PID controller, model no. CNI1654-C24-DC, may be suitable.

Referring to FIGS. 1 and 2, the fluid handling system 100 may include a flow regulator 150. The flow regulator 150 receives a pressurized working fluid 32 from the working fluid flow generator 134. Typically, the pressurized working fluid 32 received by the flow regulator 150 is pulsed and not sufficiently stable for delivery to the fluid flow instrument 10. Thus, the flow regulator 150 is controlled to adjust one or more parameters or characteristics of the working fluid 32 in order to provide a relatively constant fluid flow 34 to the fluid flow instrument 10.

Fluid delivered to the fluid flow instrument, i.e., working fluid 34, may be provided as a continuous flow or a variable (including intermittent) flow of an amount of fluid without limitation on volume, rate, pressure, duration, or the like. For example, the working fluid 34 may be intermittent with a flow rate ranging from between zero and a maximum flow rate value. In preferred embodiments, the working fluid 34 may be continuous with substantially negligible variation in one or more of the fluid flow characteristics. For example, the pressure of the working fluid 34 may be controlled within certain practical operating limits of a particular instrument such as a liquid chromatograph or flow cytometer.

Thus, according to aspect of the disclosure, one or more fluid flow characteristics of a working fluid 32 may be regulated or altered within the flow regulator 150. For example, a fluid flow pressure, a fluid flow rate, an amplitude or a frequency of a fluid pressure waveform, an amplitude or a frequency of a fluid flow rate waveform may be altered and/or controlled. As one non-limiting example, the working fluid flow generator 134 may generate pulsations in the working fluid 32 received by the flow regulator 150. These pulsations may have wave form(s) of particular frequency and amplitude. The fluid flow characteristics or parameters of the pulsation in the working fluid 32 may be regulated or altered within the flow regulator 150, as below described. Additionally, the actual level of at least one fluid flow characteristic may be assessed or measured for comparison with a pre-determined level (or desired level) of the same fluid flow characteristic.

Now referring to FIGS. 1 and 2, a working fluid flow regulator 150 may include an internal chamber 151. The internal chamber 151 may define two sub-chambers: a control fluid flow path 152 and a working fluid flow path 154 separated by a flexible barrier 155. The volume of the internal chamber 151 is a constant, whereas the volume of each of the two sub-chambers 152, 154 may vary depending upon the position, i.e., the deflection of the flexible barrier 155. The volume of the control fluid flow path 152 may correspond to the regulated control fluid volume 126 of the control fluid flow system 120. The volume of the working fluid flow path 154 may correspond to the regulated working fluid volume 136 of the working fluid flow system 130.

Referring now to FIGS. 1, 2 and 4A-4D, the working fluid flow path 154 has one or more working fluid flow inlets 154*a* and one or more working fluid flow outlets 154*b* for directing working fluid 32. The control fluid flow path 152 has one or more control fluid inlets 152*a* and may have one or more control fluid outlets 152*b* for directing control fluid flow 22. In general, the flow regulator 150 provides a working fluid flow path 154 and a control fluid flow path 152 which allows one or more of the fluid flow characteristics of the working fluid 32 to be responsive to one or more of the control fluid flow characteristics of the control fluid flow 22.

Referring back to FIGS. 1 and 2, control fluid outlet 152*b*, if any, may include a pressure release system 128 such as a pressure release valve, check valve, drain valve, bleed valve, or the like. The pressure release system 128 may be passive or actively controlled to maintain a desired level of pressure within the regulated control fluid volume 126 should the pressure rise above the desired pressure. In preferred embodiments, the pressure release system 128 may include a pressure bleed valve. Further, the pressure bleed valve may be provided as a three-way valve that includes a valve configured to stop and/or start the ingress of control fluid 22 into the control fluid flow path (e.g., the control fluid flow volume 126). Advantageously, providing inlet and/or outlet control fluid valves allows for repeatable, electronically-controlled shutdown of the control fluid flow system 120, as well as, significantly reducing the start-up time to achieve the desired substantially stable flow parameters for working fluid 34.

Again referring primarily to FIG. 1, the flow regulator 150 may include a flexible, fluid impermeable barrier 155 which fluidically isolates (i.e., seals) the working fluid flow path 154 from the control fluid flow path 152. Thus, the flexible barrier 155 may be located between the control fluid flow 22 in the control fluid volume 126 and the working fluid 32 in the working fluid volume 136. The flexible barrier 155 may flex, move, deform, etc. according to the relative pressures, volumes, flows, etc. of the control fluid flow 22 on one side of the flexible barrier 155 and the working fluid flow 32 on the other side of the flexible barrier 155. The flexible barrier 155 may be provided as a substantially planar sheet of flexible material. Typically, the flexible barrier 155 may be an inelastic flexible material which can deformed or displaced without any substantial stretching in response to an out-of-plane load exerted on the flexible barrier 155 by the working fluid flow 32 and/or the control fluid flow 22.

Thus, in certain preferred embodiments, the flexible barrier 155 does not store sufficient energy from receiving the load to return to its original shape. Rather, the flexible barrier 155 may be made of an inelastic flexible material that deforms or displaces away from the working fluid flow 32 or the control fluid flow 22, whichever exerts the greater pressure. Flexure of the flexible barrier 155 alters the configuration and volume of the regulated working fluid volume 136 and the regulated control fluid volume 126. As an example, the flexible barrier 155 may be formed from a low density polyethylene. In preferred embodiments, the flexible barrier 155 may be formed of an ethylene propylene diene monomer (EPDM) synthetic rubber membrane approximately 1.6 mm thick having a 60 durometer.

In preferred embodiments, when the flexible barrier 155 is undeformed, the regulated working fluid volume 136 may have a volume of between approximately 15 milliliters ("mL") and approximately 35 mL and the control fluid volume 126 may have a volume of between approximately 120 mL and approximately 400 mL. The ratio of the volume of the control fluid volume 126 to volume of the working fluid volume 136 may range from approximately 5 to approximately 15, more preferably from approximately 8 to approximately 12. As one example, the volume of the regulated working fluid volume 136 may be approximately 25 mL and the volume of the regulated control fluid volume 126 may be approximately 255 mL, with a ratio of control fluid volume to working fluid volume of approximately 10 to 1. During operation, the volume of the regulated working fluid volume 136 may range from approximately 10 to approximately 50 mL and the volume of the regulated control fluid volume 126 may range from approximately 100 to approximately 450 mL. These dimensions are not intended to be limiting.

In a preferred embodiment, the configuration of the internal chamber 151 and thus also of the control fluid flow path 152 and the configuration of regulated control fluid volume 126 in plan view may be circular. A circular internal chamber 151 with a circular flexible barrier 155 allows undesirable stresses in the flexible barrier 155 to be mitigated. The flexible barrier may have a diameter in the range of approximately 3 inches to approximately 9 inches. The flexible barrier 155 need not be circular and further, these dimensions are not intended to be limiting.

According to certain embodiments and referring to FIG. 2, flow regulator 150 may be oriented at a non-horizontal angle α. Specifically, the working fluid flow path 154 within flow regulator may be oriented at a non-horizontal angle α, with the working fluid inlet 154a located below or lower than the working fluid outlet 154b. In this orientation, the working fluid flow 32 must rise as it flows through the flow regulator. This non-horizontal orientation of the working fluid flow path 154 allows any undesirable air bubbles flowing within working fluid 32 to be flushed through the system and not remain trapped with the flow regulator 150. As a non-limiting example, the angle α may be at least approximately 45 degrees (i.e., plus/minus 10%). In preferred embodiments, if assembly conditions allow, the angle α may be greater than approximately 60 degrees.

Now referring to both FIGS. 1 and 2, the flow regulator 150 may further include one or more fluid parameter sensor(s) 156. The fluid parameter sensor(s) 156 may directly or indirectly sense a value of one or more flow parameters of the control fluid flow 22 and/or of the working fluid flow 32 within the flow regulator. Additionally and/or alternatively, the fluid parameter sensor(s) 156 may directly or indirectly sense a variation or change in one or more flow parameters of the control fluid flow 22 and/or of the working fluid flow 32. The fluid parameter sensor 156 may generate a fluid parameter signal 141 which varies based upon directly or indirectly sensed values and/or variations in the working fluid flow 32 in the working fluid flow path 154 and/or values and/or variations in the control fluid flow 22 in the control fluid flow path 152 within the flow regulator 150. Fluid parameters or characteristics such as pressure, volume, flow rate, temperature, etc. may be sensed.

According to one embodiment, the fluid parameter sensor 156 may generate a fluid parameter signal 141 that varies based upon movement, displacement and/or flexing of the flexible barrier 155. As a non-limiting example, the fluid parameter sensor 156 may be a Hall Effect sensor. Other fluid parameter sensors 156 known to persons of ordinary skill in the art given the benefit of this disclosure may be used.

The fluid parameter sensor 156 (e.g., a Hall Effect sensor) may be mounted on the flexible barrier 155 or on a wall of the internal chamber 151 of the flow regulator 150. As the flexible barrier 155 moves in response to the control fluid flow 22 within the control fluid volume 126 and/or the working fluid flow 32 within the working fluid volume 136, a voltage signal 141 from the Hall Effect sensor may correspondingly increase or decrease. Thus, the variation being directly sensed may be, for example, movement or flexing of the flexible barrier 155. This displacement or flexing of the flexible barrier 155 corresponds to a change in one or more flow parameters of the control fluid flow 22, the working fluid flow 32 and/or both.

According to certain aspects, the fluid parameter sensor 156 may send a signal 141 to the control system 140 that reflects a variation in a fluid parameter of the control fluid flow 22 and/or the working fluid flow 32 within the flow regulator 150. The control system 140 may control one or more fluid parameters of the control fluid flow 22 and/or one or more fluid parameters of the working fluid flow 32 to regulate or control the fluid parameters of the working fluid flow 34 exiting the flow regulator 150 and being provided to the fluid flow instrument 10.

Thus, according to some aspects, upon receiving a signal 141 indicating a change in a fluid parameter within the flow regulator 150, the fluid controller 142 may provide a signal 143 to the control fluid regulator 124 to continuously or intermittently adjust delivery of the control fluid 20. The fluid controller 142 may thereby intermittently or continuously adjust control fluid characteristics (e.g., volume, pressure, flow rate, or the like) of the control fluid flow 22 delivered from the control fluid source 122 to the flow regulator 150. The control fluid flow 22 having adjusted control fluid characteristics within the control fluid volume 126 acts on the flexible barrier 155 to thereby affect the working fluid flow 32 in the working fluid flow path 154.

Thus, according to exemplary embodiments, the control system 140 may operate to maintain the control fluid 22 within the control fluid volume 126 at a constant pressure.

For example, the pressure of the control fluid 22 within the control fluid volume 126 may be regulated to be substantially constant by controlling the pressure release system 128 (e.g., a control fluid regulator valve or other valve). For example, should the flexible barrier 155 be pushed upward into the control fluid volume 126 due to an increase in pressure within the working fluid volume 136, a signal 141 may be sent to the fluid controller 142 indicating an increase in pressure within the control fluid volume 126. In response to this signal indicating a pressure increase, the fluid controller 142 may send a signal 147 to the pressure release system 128 to allow control fluid 22 to be released from the control fluid volume 126. The release of control fluid via the pressure release system 128 may thereby allow the pressure within the control fluid volume 126 to decrease back to its nominal or desired level.

According to even other embodiments, the pressure release system 128 may be set to automatically release control fluid 22 from the control fluid volume 126 upon the pressure within the control fluid volume 126 exceeding a predetermined pressure. For example, the pressure release system 128 may be provided as a check valve or other one-way valve that does not require a signal from the fluid controller 142 to release control fluid 22 above a predetermined pressure.

According to other embodiments, the pressure of the control fluid within the control fluid volume 126 may be regulated to a substantially constant pressure by controlling the pressure and/or flow of the control fluid flow 22 entering the control fluid volume 126. Thus, for example, the fluid controller 142 may send a signal 145 (in response to receiving a signal 141 from the sensor 156) to the control fluid regulator 124 to providing additional control fluid 22 to the control fluid volume 126. For example, should the pressure within the control fluid volume 126 fall below a nominal or desired pressure level, flexible barrier 155 may flex upward into the control fluid volume 126 thereby resulting in the pressure of the working fluid 32 in the working fluid volume 136 falling below its desired pressure level (due to the increase in volume in the working fluid volume 136). A signal 141 may be sent to the fluid controller 142 indicating a decrease in pressure within the control fluid volume 126. In response to this signal, the fluid controller 142 may send a signal 145 to the control fluid regulator 124 to provide additional control fluid 22 to the control fluid volume 126. The increased flow of control fluid 22 to the control fluid volume 126 may increase the pressure within the control fluid volume back to its nominal or desired level.

Maintaining a constant pressure in the control fluid volume 126 may maintain the working fluid flow 32 in the working fluid volume 136 at a constant flow rate by displacement of the flexible barrier 155 toward the working fluid volume 136.

According to other aspects, upon receiving a sensor signal 141 indicating a change in a fluid parameter within the flow regulator 150, the fluid controller 142 may provide a signal 145 to the working fluid flow generator 134 to continuously or intermittently adjust delivery of the working fluid 30 to the flow regulator 150. The fluid controller 142 may thereby intermittently or continuously adjust fluid characteristics (e.g., volume, pressure, flow rate, or the like) of the working fluid flow 32 delivered from the working fluid source 132 to the flow regulator 150.

The fluid controller 142 may be programmed to receive and/or determine the magnitude of the sensor signal 141, a magnitude of the change in the sensor signal 141, a magnitude of the rate of change of the sensor signal 141, etc. and based on this information, provide a control signal 145 to the working fluid flow generator 134. The control signal 145 may control the absolute speed, a change in speed, a rate of change in speed, etc. of a motor of the working fluid flow generator 134.

For example, the fluid controller 142 may determine a difference between a measured value of the signal 141 and a set-point value and modify the speed of the working fluid flow generator 134. As the deviation from the set-point decreases; the change in control signal 145 also decreases. The change in the control signal 145 may be determine based on a weighted summation of this difference, a summation of past differences and rate of change of the difference (i.e., a PID controller). According to some embodiments, the change in the control signal 145 may be determine based on a weighted summation of the present difference and a summation of past differences (i.e., a PID controller with the derivative term set to zero). Removing the derivative term may provide a slower, but more stable response to perturbations.

The flow regulator 150, even without active control, may have a relatively substantial inherent damping capability. As such, use of a PID controller having a sampling rate of approximately 3 times per second may provide sufficient control with minimal, if any, overshoot, oscillation and/or hunting for the set-point. In a preferred embodiment, the frequency at which the fluid controller 142 reads the sensor signal 141 is greater than a frequency of the pulsed flow of the working fluid 32 supplied to the working fluid volume 136 of the flow regulator 150. Further, when paired with the disclosed flow regulator 150, use of a PID controller may result in short transients and/or high stability being achieved.

As even another example, the fluid controller 142 may provide control signals 145 based on whether the signal 141 received from the sensor 156 is within a predetermined range and whether or not the rate of change of the sensor signal 141 is positive or negative. The predetermined range of the sensor signal 141 may reflect whether a fluid parameter is above or below a nominal or desired value of the fluid parameter. Thus, the fluid controller 142 may have a first logic associated with a first sensor signal 141 range (corresponding to a first fluid parameter range) and a second logic associated with a second sensor signal 141 range (corresponding to a second fluid parameter range).

Thus, according to some aspects, a method of controlling a fluid handling system 100 to supply a working fluid 30 to a fluid flow instrument 10 may include receiving a sensor signal 141 from a sensor 156 indicative of a deformation of a flexible barrier 155 located between a control fluid volume 126 containing a control fluid 22 and a working fluid volume 136 containing the working fluid 32. For example, a controller 142 may receive a first sensor signal 141 from the sensor 145 indicative of a first deformation of the flexible barrier 155. The controller 142 may further receive a second sensor signal 141 from the sensor 145 indicative of a second deformation of the flexible barrier 155. The controller 142 may be programmed to determine if the flexible barrier 155 is deformed toward the control fluid volume 126 or if the flexible barrier 155 is deformed toward the working fluid volume 136. The controller 142 may further be programmed to determine if the deformation of the flexible barrier 155 is increasing.

The method may include sending a control signal 145 to a working fluid flow generator 134 positioned upstream of the working fluid volume 136. The control signal 145 may be determined as a function of the sensor signal(s) 141. For example, when the flexible barrier 155 is deformed toward the working fluid volume 136 and when the deformation of the flexible barrier 155 is increasing, the control signal 145 may be configured to increase a flow rate of the working fluid 32 supplied to the working fluid volume 136. As another example, when the flexible barrier 155 is deformed toward the control fluid volume 126 and when the deformation of the flexible barrier 155 is increasing, the control signal 145 may be configured to decrease the flow rate of the working fluid 32 supplied to the working fluid volume 136. These control actions may result in the flexible barrier 155 moving back toward an undeformed equilibrium position. When the flexible barrier 155 is undeflected, the value of the sensor signal 141 may be defined as the nominal signal value.

The method may also include providing the control fluid 22 to the control fluid volume 126 at a constant pressure.

According to some embodiments, the control signal 145 may be proportional to a change in the value of the sensor signal 141 from the previous sensor signal value. Alternatively, the control signal 145 may be proportional to a difference in the sensor signal 141 from a predetermined and/or nominal sensor signal value. As yet another example, the control signal 145 may be a function of a rate of change of the sensor signal 141.

For example, a pressure increase within the working fluid volume 136 may cause the flexible barrier 155 to move upward. According to an embodiment wherein a Hall Effect sensor is used to track movement of the flexible barrier 155, a signal 141 (e.g., a voltage) from the Hall Effect sensor reflecting this movement may be sent to fluid controller 142 (e.g., a PID) from sensor 156. In turn, a signal 145 may be sent from the PID to the working fluid flow generator 134 to slow down and reduce the flow rate into the working fluid volume 136. If the flow rate of the working fluid flow 34 exiting the flow regulator 150 is greater than the flow rate of the working fluid flow 32 entering the flow regulator 150, the pressure within the working fluid volume 136 decreases back to its nominal or desired level.

As the flexible barrier 155 moves back to its neutral position, the fluid parameter sensor 156 may send signals 141 to fluid controller 142, which in turn may send signals 145 to the working fluid flow generator 134. The working fluid flow generator 134 may then allow the flow rate of the working fluid flow 32 to return to its nominal rate (i.e., to the same flow rate as the working fluid 34 exiting the flow regulator 155. In other words, the fluid parameter sensor 156 may generate signal variation values 141 and sends these signals 141 to fluid controller 142. Fluid controller 142 may generate working fluid flow generator adjustment signals 145, based on input from signals 141, and sends these adjustment signals 145 to working fluid flow generator 134. The operation of the working fluid flow generator 134 is thereby regulated so as to maintain a substantially constant amount of working fluid at a substantially constant pressure in the working fluid volume 136 of the flow regulator 150.

According to the above control algorithms, working fluid flow 34 exiting from the flow regulator 150 may have a substantially constant flow rate and/or a substantially constant pressure profile, while the incoming working fluid flow 32 entering into working fluid volume 136 of the flow regulator 150 may have a variable flow rate and/or a variable pressure profile. The variable flow rate and/or variable pressure profile of the incoming working fluid 32 may be an artifact of the operation of the working fluid flow generator 134. Thus, the flow regulator 150 decreases or attenuates variations in flow parameters of the incoming working fluid 32. According to certain embodiments, the flow regulator 150 may attenuate an incoming pressure pulse to an outgoing pressure pulse below approximately 0.010 psi (peak-to-peak). In even other embodiments, the flow regulator 150 may attenuate an incoming pressure pulse to an outgoing pulse below approximately 0.005 psi (peak-to-peak). In one exemplary embodiment, the flow regulator 150 attenuated an incoming pressure pulse of approximately 4 psi (peak-to-peak) to an outgoing pressure pulse of approximately 0.003 psi (peak-to-peak).

Thus, according to certain preferred embodiments, upon receiving a signal 141 indicating a change in a fluid parameter of the working fluid flow 32 within the flow regulator 150, the fluid controller 142 may provide an adjustment signal 145 to the working fluid flow generator 134 to continuously or intermittently control delivery of the working fluid 30. For example, the fluid controller 142 may provide an adjustment signal 145 to control the rate that working fluid 32 is delivered to the flow regulator 150. Specifically, as a non-limiting example, the adjustment signal 145 may control the speed of a peristaltic pump 134a.

According to even other aspects, the control system 140 may be used to monitor the fluid handling system for clogs or other operational anomalies. Thus, according to certain embodiments and referring to FIG. 2, a fluid handling system 100, as described above, may further include an operation sensor 135 coupled to the working fluid flow generator 134 and configured to monitor the operation of the generator 134. The operation sensor 135 may be configured to sense variations in operational characteristics (temperature, motor speed/rpm, rotor speed/rpm, power draw, vibrations, acoustics, etc.) of the working fluid flow generator 134. The operation sensor 135 may be configured to transmit a signal 144 to the control system 140 on a continuous or quasi-continuous basis.

In certain embodiments, the control system 140 may be configured to monitor the signal 144 and send an alarm or an alert signal or even a shut-down signal if a predetermined variation or change in an operational characteristic of a component or system of the fluid handling system 100 is sensed. For example, if operation sensor 135 senses or registers a step change, quasi-step change, or other unexpectedly large variation or change in an operational characteristic of the working fluid flow generator 134 over a relatively short time span, this may indicate a clog or partial clog in the flow through the fluid flow instrument, a leak in the fluid handling system, etc. Other anomalies in the operation of the fluid handling system 100 may occur over a longer time frame and may indicate a general degradation of the system or components within the system (e.g., peristaltic pump tubes needing to be replaced, etc.). The value associated with a predetermined change in the operation characteristic that triggers an alert, an alarm, or a shut-down need not be the same.

In some embodiments, the signal 144 sent to the control system 140 from the operation sensor 135 may be monitored for unexpected behavior relative to a signal 141 sent to the control system 140 from the fluid variation sensor 156. When the fluid handling system 100 is functioning properly, the signal 141 sent to the control system 140 from the fluid variation sensor 156 may settle into a substantially regular, relatively narrow-band fluctuation around a nominal value (e.g., a signal reflecting less than a 0.010 psi peak-to-peak pressure pulse fluctuation). Similarly, during such a steady-state condition, the signal 145 sent to the working fluid flow generator 143 from the fluid controller 142 may settle into a substantially regular, relatively narrow-band fluctuation around a nominal value. A steady-state or stable condition may be defined as an operating state wherein the value and/or variation in the signal 141 is less than a predetermined level (e.g., less than a 5% fluctuation around a nominal value, or less than a 2% fluctuation around a nominal value, etc.). Thus, for example, control system 140 may be configured to send an alert if the signal 144 from the operation sensor 135 undergoes a step change, quasi-step change, or other unexpectedly large variation or change over a relatively short time span or a drift in a nominal value over a longer time frame, while at the same time the signal 141 from the sensor 156 remains relatively stable.

In certain other embodiments, the control system 140 may be configured to compare a change in the signal 145 sent to working fluid flow generator 134 to a change in the signal 144 received from the working fluid flow generator operation sensor 135.

FIGS. 5A-5C illustrate various components of a fluid handling system 100 packaged within a housing 170. The housing 170 may include a removable top panel 172 and/or a removable portion 174 of the back panel to facilitate access to the various components. The front panel of the housing 170 may include any of various gauges (e.g., a control fluid pressure gauge, etc.), displays or knobs (e.g., a control fluid regulator knob, etc.) for monitoring the operation of the fluid handling system 100. The back panel may include fluidic inlet ports, fluid outlet ports, power inputs, control inputs/outputs, gauges (e.g., a vacuum gauge, if any, etc.) and/or displays. Further, a fan may be mounted to the back panel to assist in controlling the temperatures of the components of the fluid handling system 100. FIG. 5A shows that flow regulator 150 may be mounted at an angle from the horizontal.

During operation of the fluid handling system 100, the fluid variation sensor 156 may sense values and/or variations in a working fluid characteristic (pressure, flow in, flow out, temperature, volume, height, etc.) within the flow regulator 150 and sends signals 141 corresponding to these values and/or variations to fluid controller 142. In turn, the fluid controller 142 may send signals 145 to the working fluid flow generator 134. The operation of working fluid flow generator 134 may be adjusted (e.g., the motor speed may be increased, decreased, stopped and/or started) so as to regulate or control the fluid characteristic of the working fluid 34 being provided to the fluid flow instrument 10.

According to certain aspects, a fluid handling system 100 may supply working fluid 30 to a plurality of fluid flow instruments 10. For example, working fluid 34 from a single flow regulator 150 may be supplied to a plurality of fluid flow instruments 10. Additionally and/or alternatively, a fluid handling system 100 may be provided with a plurality of flow regulators 150 and each flow regulator 150 may supply regulated working fluid 34 to one or more fluid flow instruments 10. The working fluid 30 may be a sheath fluid, a sample fluid, a reagent fluid, etc.

While the present disclosure has described specific examples including presently preferred modes of carrying out the disclosed systems and methods, those skilled in the art will appreciate that there are numerous variations and permutations of the above described systems and methods. Thus, the spirit and scope of the invention should be construed broadly as set forth in the appended claims.

The invention claimed is:

1. A method of controlling a fluid handling system to supply a working fluid to a fluid flow instrument, the method comprising:
   receiving a compressible control fluid into a control fluid volume of a flow regulator;
   supplying a first quantity of a substantially incompressible working fluid having a first pulse peak-to-peak value from a peristaltic pump to a working fluid volume of the flow regulator, the peristaltic pump having a first rotor and a second rotor attached to a common drive shaft, wherein shoes attached to the first rotor are rotationally staggered from shoes attached to the second rotor;
   sending a sensor signal from a sensor to a controller, the sensor signal indicative of a position of a flexible barrier located between the control fluid volume containing the control fluid and the substantially incompressible working fluid volume containing the working fluid;
   sending a control signal from the controller to the peristaltic pump;
   controlling the peristaltic pump;
   discharging a second quantity of the substantially incompressible working fluid having a second pulse peak-to-peak value from the working fluid volume of the flow regulator;
   wherein the second pulse peak-to-peak value is less than the first pulse peak-to-peak value, and
   wherein the control signal is determined, at least in part, as a function of the difference between the sensed position of the flexible barrier and a nominal position of the flexible barrier.

2. The method of claim 1,
   wherein the substantially incompressible working fluid entering the working fluid volume has a nominal pressure of between approximately 40 psi to approximately 50 psi with a pressure pulse fluctuation of at least 2 psi (peak-to-peak), and
   wherein the substantially incompressible working fluid exiting the working fluid volume has a nominal pressure of between approximately 40 psi to approximately 50 psi with a pressure pulse fluctuation of less than 0.010 psi (peak-to-peak).

3. The method of claim 1, wherein the substantially incompressible working fluid entering the working fluid volume has a nominal pressure of between approximately 40 psi to approximately 50 psi with a pressure pulse fluctuation of at least 2 psi (peak-to-peak), and
   wherein the substantially incompressible working fluid exiting the working fluid volume has a nominal pressure of between approximately 40 psi to approximately 50 psi with a pressure pulse fluctuation of less than 0.005 psi (peak-to-peak).

4. The method of claim 1, wherein the control fluid is supplied to the control fluid volume at a substantially constant pressure of between approximately 40 psi to approximately 50 psi.

5. The method of claim 1, wherein a pressure release valve is in fluid communication with the control fluid volume of the flow regulator.

6. The method of claim 1, wherein the controller is a PID controller.

7. The method of claim 1, wherein the controller is a PID controller, and wherein the derivative term of the PID controller has a zero coefficient.

8. The method of claim 1, wherein the volume of the control fluid volume is greater than 200 mL.

9. The method of claim 1, wherein the volume of the control fluid volume is greater than approximately 200 mL and wherein the volume of the working fluid volume is between approximately 15 mL and approximately 35 mL.

10. The method of claim 1, wherein the ratio of the volume of the control fluid volume to the volume of the working fluid volume is between approximately 8 and approximately 12.

11. The method of claim 1, wherein the flexible barrier is circular.

12. The method of claim 1, wherein the flexible barrier is formed of EPDM.

13. The method of claim 1, wherein the flexible barrier is positioned at a non-zero angle to the horizontal.

14. The method of claim 1, wherein the control signal is a function of the difference in the sensor signal value from a predetermined nominal sensor signal value and of the accumulated difference in the sensor signal value from a predetermined nominal sensor signal value.

15. The method of claim 1, wherein the sensor signal value reflects the difference from a predetermined nominal sensor signal and the control signal is a weighted sum of the sensor signal and an accumulation of previous sensor signal values.

16. The method of claim 1, wherein the controller reads the sensor signal at least approximately three times per second.

17. The method of claim 1, wherein the controller reads the sensor signal at a greater frequency than a frequency of the pulsed flow of the substantially incompressible working fluid supplied to the working fluid volume of the flow regulator.

18. A fluid handling system comprising:
a peristaltic pump having a first rotor and a second rotor attached to a common drive shaft with shoes attached to the first rotor rotationally staggered from shoes attached to the second rotor;
a flow regulator having a control fluid volume to receive a compressible control fluid, a working fluid volume to receive a substantially incompressible working fluid, and a flexible barrier positioned between the control fluid volume and the working fluid volume;
a sensor to provide a sensor signal indicative of a position of the flexible barrier; and
a controller to receive the sensor signal from the sensor, the controller providing control signals to the peristaltic pump that are determined, at least in part, as a function of the difference between the sensed position of the flexible barrier and a nominal position of the flexible barrier,
wherein the peristaltic pump supplies a first quantity of substantially incompressible working fluid having a first pulse peak-to-peak value to the working fluid volume of the flow regulator; and
wherein the controller controls the peristaltic pump to discharge a second quantity of the substantially incompressible working fluid having a second pulse peak-to-peak value that is less than the first pulse peak-to-peak value.

19. The fluid handling system of claim 18, wherein, during operation, the working fluid volume is completely filled with the substantially incompressible working fluid.

20. The fluid handling system of claim 18, wherein the substantially incompressible working fluid entering the working fluid volume has a nominal pressure of between approximately 40 psi to approximately 50 psi with a pressure pulse fluctuation of at least 2 psi (peak-to-peak), and
wherein the substantially incompressible working fluid exiting the working fluid volume has a nominal pressure of between approximately 40 psi to approximately 50 psi with a pressure pulse fluctuation of less than 0.010 psi (peak-to-peak).

21. The fluid handling system of claim 18, wherein the substantially incompressible working fluid entering the working fluid volume has a nominal pressure of between approximately 40 psi to approximately 50 psi with a pressure pulse fluctuation of at least 2 psi (peak-to-peak), and
wherein the substantially incompressible working fluid exiting the working fluid volume has a nominal pressure of between approximately 40 psi to approximately 50 psi with a pressure pulse fluctuation of less than 0.005 psi (peak-to-peak).

22. The fluid handling system of claim 18, wherein the control fluid is supplied to the control fluid volume at a substantially constant pressure of between approximately 40 psi to approximately 50 psi.

23. The fluid handling system of claim 18, further comprising a pressure release valve in fluid communication with the control fluid volume of the flow regulator.

24. The fluid handling system of claim 18, wherein the controller is a PID controller.

25. The fluid handling system of claim 18, wherein the controller is a PID controller, and wherein the derivative term of the PID controller has a zero coefficient.

* * * * *